US006977379B2

(12) United States Patent
Zhang et al.

(10) Patent No.: US 6,977,379 B2
(45) Date of Patent: Dec. 20, 2005

(54) T-RAY MICROSCOPE

(75) Inventors: Xi-Cheng Zhang, Latham, NY (US); Jingzhou Xu, Troy, NY (US); Tao Yuan, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 258 days.

(21) Appl. No.: 10/434,329

(22) Filed: May 8, 2003

(65) Prior Publication Data

US 2005/0230625 A1    Oct. 20, 2005

Related U.S. Application Data

(60) Provisional application No. 60/379,569, filed on May 10, 2002.

(51) Int. Cl.⁷ ............................................. G01N 21/35
(52) U.S. Cl. .................................................... 250/341.1
(58) Field of Search ...................................... 250/341.1

(56) References Cited

U.S. PATENT DOCUMENTS

| | | |
|---|---|---|
| 5,406,194 A | 4/1995 | Dykaar et al. |
| 5,497,359 A | 3/1996 | Mamin et al. |
| 5,519,212 A | 5/1996 | Elings et al. |
| 5,581,082 A | 12/1996 | Hansma et al. |
| 5,596,401 A | 1/1997 | Kusuzawa |
| 5,710,430 A | 1/1998 | Nuss |
| 5,729,017 A | 3/1998 | Brener et al. |
| 5,770,856 A | 6/1998 | Fillard et al. |
| 5,789,750 A | 8/1998 | Nuss |
| 5,894,125 A | 4/1999 | Brener et al. |
| 5,936,237 A | 8/1999 | van der Weide |
| 5,952,818 A | 9/1999 | Zhang et al. |
| 6,100,703 A | 8/2000 | Davidov et al. |
| 6,111,416 A | 8/2000 | Zhang et al. |
| 6,476,596 B1 * | 11/2002 | Wraback et al. .......... 324/158.1 |
| 6,828,558 B1 * | 12/2004 | Arnone et al. ........... 250/341.1 |
| 2001/0038074 A1 * | 11/2001 | Zhang et al. ............. 250/341.8 |
| 2002/0153874 A1 | 10/2002 | Zhiping et al. |
| 2004/0155665 A1 * | 8/2004 | Arnone et al. .............. 324/644 |

FOREIGN PATENT DOCUMENTS

| | | | |
|---|---|---|---|
| DE | 100 54 476 A1 | 1/2002 | |
| GB | 2 347 835 A | 9/2000 | |
| WO | WO 200075641 A1 * | 12/2000 | ............. G01J 5/02 |

OTHER PUBLICATIONS

Q. Cheng, Zhiping Jiang, G. X. Xu, X.-C. Zhang; "Near-field terahertz imaging with a dynamic aperture"; Optics Letters, vol. 25, No. 15; Aug. 1, 2000; pp. 1122-1124.

(Continued)

Primary Examiner—Constantine Hannaher
(74) Attorney, Agent, or Firm—RatnerPrestia

(57) ABSTRACT

A microscope for producing an image of a target using THz radiation. The microscope comprises a source for providing an optical pump pulse and an optical probe pulse; a THz emitter for activation by pump pulse to emit a THz pulse that irradiates the target to form a target-modified THz pulse; a THz detector for modulating the probe pulse with the target-modified THz pulse to create a modulated optical probe pulse characteristic of the target; an optical detection system for modifying and detecting the modulated optical probe pulse and converting the modulated optical probe pulse to electronic information; and a processor for receiving the electronic information and producing an image of the sample using the electronic information. The THz emitter and detector comprise one or more EO crystals. The target is positioned on one of the EO crystals in a near-field of the THz pulse.

38 Claims, 3 Drawing Sheets

OTHER PUBLICATIONS

Q. WU, F. G. Sun, P. Campbell, X,-C. Zhang; "Dynamic range of an electro-optic field sensor and its imaging applications"; Appl. Phys. Lett. 68 (23); June 3, 1996; pp. 3224-3226.

P. Y. Han, G. C. Cho, X.-C. Zhang; "Time-domain transillumination of biological tissues with terahertz pulses"; Optics Letters, vol. 25, No. 4; Feb. 15, 2000; pp. 242-244.

Z. G. Lu, P. Campbell, X.-C. Zhang; Free-space electro-optic sampling with a high-repetition-rate regenerative amplified laser; Appl. Phys. Lett 72 (5); Aug. 4, 1997; pp 593-595.

Q. Wu, T. D. Hewitt, X.-C. Zhang; "Two-dimensional electro-optic imaging of THz beams"; Appl. Phys. Lett. 69 (8); Aug. 19, 1996; pp. 1026-1028.

Daniel M. Mittleman, Stefan Hunsche, Luc Boivin, Martin C. Nuss; "T-ray tomography"; Optics Letters, vol. 22, No. 12; Jun. 15, 1997; pp. 904-906.

Daniel M. Mittleman, Rune H. Jacobsen, Martin C. Nuss; "T-Ray Imaging"; IEEE Journal of Selected Topics in Quantum Electronics, vol. 2, No. 3; Sep. 1996; pp. 679-692.

Q. Mitrofanov, R Harel, M. Lee, L. N. Pfeiffer, K. West, J. D. Wynn, J. Federici; "Study of single-cycle pulse propagation inside a terahertz near-field probe"; Applied Physics Letters, vol. 78, No. 2; Jan. 8, 2001; pp. 252-254.

S. V. Frolov, Z. V. Vardeny; "Double-modulation electro-optic sampling for pump-and-probe ultrafast correlation measurements"; Review of Scientific Instruments, vol. 69, No. 3; Mar. 1998, pp. 1257-1260.

S. Hunsche, M. Koch, I. Brener, M. C. Nuss; "Thz near-field imaging"; Optics Communications 150 (1998); May 1, 1998; pp. 22-26.

B. B. Hu, M. C. Nuss; "Imaging with terahertz waves"; Optics Letters, vol. 20, No. 16; Aug. 16, 1995; pp. 1716-1718.

B. Rosner, J. Peck, D. Van Der Weide, Near-Field Antennas Integrated With Scanning Probes for THz to Visible Microscopy: Scale Modeling and Limitations on Performance; IEEE Transactions on Antennas and Progagation, vol. 50, No. 5, May 2002, Published—University of Wisconsin-Madison, Wi.

O. Mitrofanov, I. Brener, Harel, J. D. Wynn, L. N. Pfeiffer, and K. W. West, J. Federici; Terahertz Near-Field Microscopy Based On A Collection Mode Detector; vol. 77, No. 22, Nov. 27, 2000.

S. Mickan, D. Abbott, J. Munch, X.-C. Zhang, T. Van Doorn; Analysis of System Trade-Offs For Terahertz Imaging, Microelectronics Journal 31, (2000) pp. 503-514.

International Search Report, not a publication.

* cited by examiner

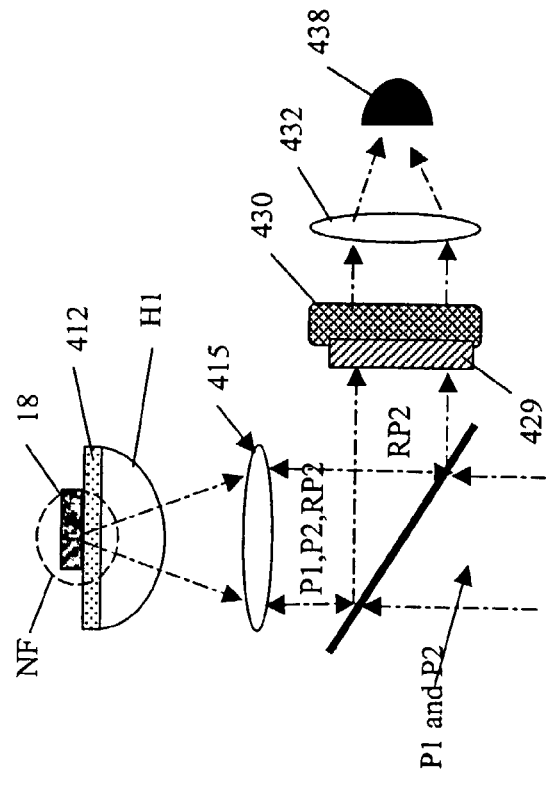
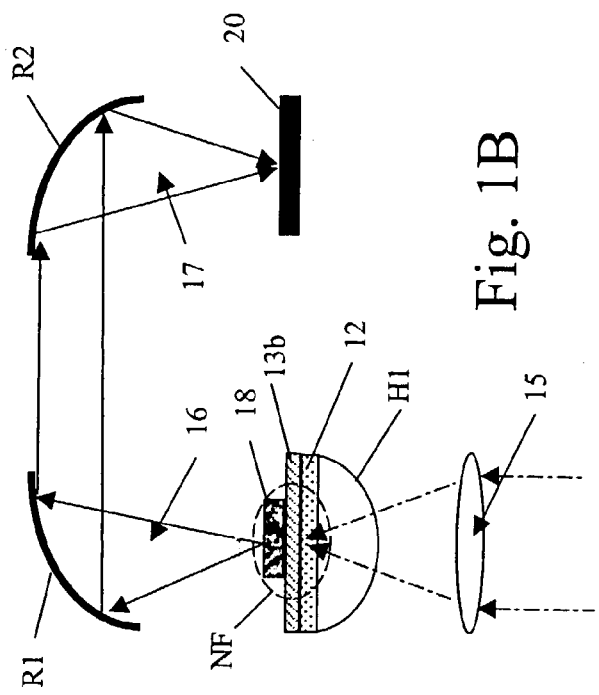
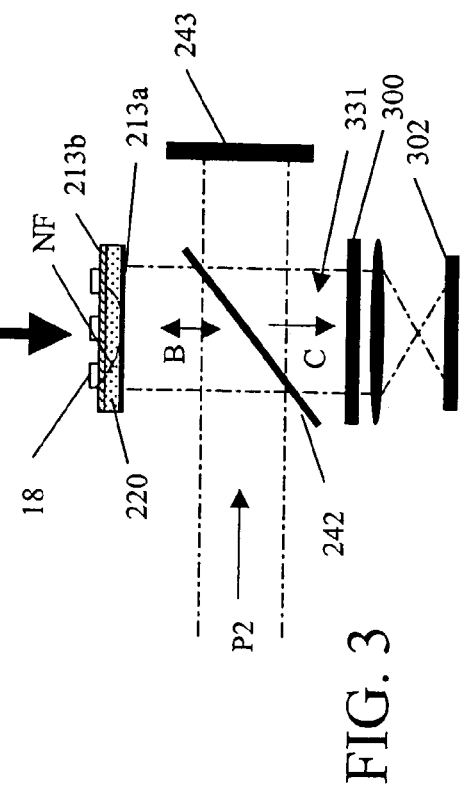
Fig. 1B
FIG. 3
FIG. 4

T-RAY MICROSCOPE

RELATED APPLICATIONS

This application claims priority of U.S. Provisional Application Ser. No. 60/379,569, filed on May 10, 2002, the contents of which are incorporated herein by reference.

GOVERNMENT FUNDING

The U.S. Government has a paid-up license in the present invention and the right in limited circumstances to require the patent owner to license others on reasonable terms as provided for by the terms of a contract awarded by the U.S. Army Research Office under funding numbers DAAD199910333 and DAAD1999C0045.

TECHNICAL FIELD

The present invention relates generally to microscopes and microscopy and, more specifically, to subwavelength imaging in the terahertz (THz) frequency range.

BACKGROUND OF THE INVENTION

THz radiation (T-rays) occupies a large portion of the electromagnetic spectrum between the infrared and microwave bands, namely the frequency interval from 0.1 to 10 THz, and is a developing frontier in imaging science and technology. In contrast to the relatively well-developed techniques for medical imaging at microwave and optical frequencies, however, there has been only limited basic research, new initiatives and advanced technology developments in the THz band. THz waves have been increasingly used to characterize the electronic, vibrational and compositional properties of solid, liquid and gas phase materials.

Unlike X-rays, T-rays have low-photon energies (4 meV @ 1 THz), low average power (nW to $\mu$W) and do not subject biological tissue to harmful radiation. T-rays can be focused to give sharper pictures. In addition, T-rays give spectroscopic information about the chemical composition as well as the shape and location of the targets they are imaging. This combination of information of the physical and the biochemical nature of the imaged tissue may be of particular value for clear and early diagnosis and detection of diseases such as cancer, allowing for a choice of treatment options.

Unlike common optical spectroscopes, which only measure the intensity of light at specific frequencies, THz time-domain spectroscopic techniques directly measure the THz wave's temporal electric field. Fourier transformation of this time-domain data gives the amplitude and phase of the THz wave pulse, therefore providing the real and imaginary parts of the dielectric constant without the use of the Kramers-Kronig relations. This allows precise measurements of the refractive index and absorption coefficient of samples that interact with the THz waves. Many rotational and vibrational spectra of various liquid and gas molecules lie within the THz frequency band, and their unique resonance lines in the THz wave spectrum allow us to identify their molecular structures. Raman spectroscopy directly uses the frequency domain to fingerprint the lattice vibrations. Similarly, THz wave spectroscopy describes molecular rotational and vibrational spectra from 10 GHz to 10 THz using the real and imaginary parts of the dielectric function that are obtained by measuring the THz wave in the time-domain. Current optical or microwave techniques cannot achieve this functionality.

Due to the diffraction-limit, the standard imaging resolution for 1 THz has historically not been much smaller than 300 $\mu$m. Near-field imaging techniques are known that can greatly improve the spatial resolution of a THz wave sensing and imaging system. Collection mode near-field imaging has been demonstrated to improve spatial resolution as low as a 7 $\mu$m imaging resolution with 0.5 THz pulses. A limitation of such a system, however, is the extremely low throughput of the THz wave past the emitter aperture, because the throughput THz wave field is inversely proportional to the third power of the aperture size of the emitter aperture. Therefore, pre-existing THz wave generation and detection technologies are inadequate for obtaining sub-micron spatial resolution.

A newly developed dynamic-aperture method with the introduction of a third gating beam can image objects with a sub-wavelength resolution ($\lambda$/100), but the drawback of this method is the difficulty in coating a gating material on the surface of biomedical samples such as cells and tissues.

Thus, there is a need in the art for a T-ray imaging technique and system that can provide imaging with sub-micron resolution using THz radiation.

SUMMARY OF THE INVENTION

One aspect of the invention comprises a microscope for producing an image of a target, the microscope comprising:
   a source for providing an optical pump pulse and an optical probe pulse;
   a THz emitter having a first surface and a second surface substantially parallel and opposite said first surface and a THz detector also having a first surface and a second surface substantially parallel and opposite said first surface;
   means for impinging said pump beam onto said THz emitter through said first surface of said emitter;
   means for impinging said probe beam onto said detector through said first surface of said detector;
   wherein at least one of said means for impinging said pump beam and said probe beam comprise an optical focusing means for focusing one of said pump beam and said probe beam to a substantially optical wave length limited spot size; and
   wherein at least one of said second surface of said emitter and said second surface of said detector is adapted to receive a sample within a near field of said THz radiation.

In a particular embodiment of the invention, the invention comprises a microscope for producing an image of a target, wherein the microscope comprises:
   a source for providing an optical pump pulse and an optical probe pulse;
   a THz emitter for activation by the optical pump pulse to emit a THz pulse that irradiates the target to form of a target-modified THz pulse said THz emitter comprising an EO crystal having first, pump beam side, surface and a second, target side surface, opposite said first surface the target side surface adapted to support said target within a near field of said THz irradiated pulse;
   a focal lens for focusing at least said pump beam onto said THz emitter;
   one of a hemispherical lens or super-hemispherical lens between said focal lens and said emitter in contact with said first surface;
   a THz detector for modulating the probe pulse with the target-modified THz pulse to create a modulated optical probe pulse characteristic of the target;

an optical detection system for modifying and detecting the modulated optical probe pulse and converting the modulated optical probe pulse to electronic information;

a processor for receiving the electronic information and producing an image of the sample using the electronic information.

The THz emitter and the THz detector may comprise a single THz transceiver, and the target-modified THz pulse may comprise a reflected component. The THz emitter may comprise a first EO crystal and the THz detector comprises a second EO crystal, and the target-modified THz pulse comprises a transmitted component. The target may be placed on a top surface of the THz emitter, and the pump beam may be directed to the THz emitter from underneath the emitter. In another embodiment, the target may be placed on a top surface of the THz detector, the THz pulse directed to the THz detector from above the detector, and the probe beam directed to the THz detector from underneath the detector.

The microscope may further comprise noise reduction components. The noise reduction components comprise a first modulator for modulating the pump beam at a first frequency and integrated with a first lock-in amplifier positioned between the optical detector and the processor. The noise reduction components may further comprise a second modulator for modulating the probe beam at a second frequency and integrated with a second lock-in amplifier connected in series with the first lock-in amplifier. The first frequency may be greater than or equal to about 1 MHz and the second frequency may be greater than or equal to about 1 kHz.

The microscope may further comprise a delay stage positioned in a pathway of one of the pump pulse or the probe pulse for enabling characterization of a complete waveform of the THz pulse. In another embodiment, optical detection system may comprise a Charge Coupled Device (CCD) camera. The microscope may further comprise means for scanning the target across an x-y plane.

The microscope may comprise a focal lens through which at least the pump beam is focused onto the THz emitter, the focal lens comprising an optical microscope objective in optical alignment with an optical microscope eyepiece to provide optical monitoring of the sample.

The microscope may further comprising a focal lens through which the pump beam and probe beam are focused onto the THz transceiver and a hemispherical lens between the focal lens and the THz transceiver, the hemispherical lens having an index of refraction that is the same as an index of refraction of the THz transceiver, the hemispherical lens and the focal lens having identical numerical apertures. Preferably a super-hemispherical lens is used as a solid immersion lens. The laser may be a Ti:sapphire laser. The one or more EO crystals may comprise ZnTe or LiNbO$_3$.

The microscope may further comprise a vacuum chamber in which at least the target and the THz emitter and/or THz detector are located.

In another embodiment, the THz emitter comprises an EO crystal having a top surface and an optically-reflective coating, such as GaAs, on the top surface. The EO crystal also may comprise a bottom surface and an anti-reflective coating on the bottom surface. The EO crystal may further comprise a conductive coating, such as gold, over the reflective coating, the conductive coating having at least one aperture therein.

The EO crystal may comprise a top surface, a conductive coating on the top surface, and at least one aperture in the conductive coating.

In another aspect of the invention, a microscope may comprise a source for providing an optical pump pulse and an optical probe pulse; a THz transceiver comprising an EO crystal having a first surface adapted for contacting the target and having an index of refraction, the THz transceiver adapted to generate a THz pulse when activated by the optical pump pulse and to modulate the optical probe pulse with a reflection of the THz pulse off of the target, creating a reflected modulated optical probe pulse; a hemispherical lens mounted on a second surface of the EO crystal opposite the first surface, having an index of refraction identical to the index of refraction of the EO crystal, and having a numerical aperture; a focal lens adapted to focus the optical pump pulse and optical probe pulse onto the hemispherical lens, the focal lens having a numerical aperture identical to the numerical aperture of the hemispherical lens; a polarizer adapted to receive, isolate, and analyze the reflected modulated optical probe pulse; an optical detection system for modifying and detecting the modulated optical probe pulse and converting the modulated optical probe pulse to electronic information; and a processor for receiving the electronic information and producing an image of the sample using the electronic information.

Still another aspect comprises a microscope comprising: a source for providing an optical pump pulse and an optical probe pulse; a THz emitter comprising an EO crystal adapted to generate a THz pulse when activated by the optical pump pulse and having a first surface for receiving the target; a focal lens through which the optical pump pulse is focused onto the THz emitter; a THz detector comprising an EO crystal adapted to receive a target-modified THz pulse produced by transmission of the THz pulse through the target and to modulate the optical probe pulse with the target-modified THz pulse to produce a modulated optical probe pulse; an optical detection system for modifying and detecting the modulated optical probe pulse and converting the modulated optical probe pulse to electronic information; and a processor for receiving the electronic information and producing an image of the sample using the electronic information.

Yet another aspect of the invention comprises a microscope comprising: a source for providing an optical pump pulse and an optical probe pulse; a THz emitter comprising an EO crystal adapted to generate a THz pulse when activated by the optical pump pulse; a THz detector comprising an EO crystal having a first side coated with a reflective coating and adapted to receive the target, and a second side coated with an anti-reflective coating, the THz detector adapted to receive the THz pulse as modified by the target from the first side, to receive an optical probe pulse from the second side, and to modulate the optical probe pulse with the THz pulse as modified by the target to produce a modulated optical probe pulse; an optical detection system for modifying and detecting the modulated optical probe pulse and converting the modulated optical probe pulse to electronic information; and a processor for receiving the electronic information and producing an image of the sample using the electronic information.

The T-ray microscope may further comprise a conductive coating over the reflective coating, the conductive coating having at least one aperture. The microscope may also further comprise a focal lens for focusing the optical probe pulse on the THz detector and means for providing an x-y scan of the target. In another embodiment the optical probe pulse may have a relatively large beam waist illuminating the target, and the optical detection system comprises a Charge Coupled Device (CCD) camera.

Yet another aspect of the invention is a method for a microscopic examination of a target using T-rays, the method comprising:

(a) providing an optical pump pulse and an optical probe pulse along a pump optical path and a probe optical path; focusing said optical pump pulse onto a THz emitter comprising an EO crystal, by transmitting said optical pump pulse along said pump optical path through a an optical means to an optical spot size limited by the optical probe pulse wavelength on a first surface of said EO crystal thereby emitting a THz radiation pulse from said THz transmitter having a THz radiation near field resolution substantially the same as said optical spot size;

(b) positioning said target in said THz radiation near field and transmitting or reflecting the THz pulse through or off of the target, creating a target-modified THz pulse;

(c) modulating the probe pulse with the target-modified THz pulse in a THz detector EO crystal to create a modulated optical probe pulse characteristic of the target;

(d) modifying and detecting the modulated optical probe pulse and converting the modulated optical probe pulse to electronic information; and (e) receiving and processing the electronic information to produce a microscopic image of the target.

Still another aspect of the invention comprises a method for a microscopic examination of a target using T-rays, the method comprising:

(a) providing an optical pump pulse and an optical probe pulse along a pump optical path and a probe optical path; focusing said optical pump pulse onto a THz emitter comprising an EO crystal, by transmitting said optical pump pulse along said pump optical path through a focal lens and one of a hemispherical or super hemispherical lens located on a first surface of said EO crystal thereby emitting a THz pulse from said THz transmitter wherein said hemispherical or super hemispherical lens has a refractive index substantially the same as the refractive index of said EO crystal;

(b) positioning said target in a near field of said THz pulse and transmitting or reflecting the THz pulse through or off of the target, creating a target-modified THz pulse;

(c) modulating the probe pulse with the target-modified THz pulse in a THz detector EO crystal to create a modulated optical probe pulse characteristic of the target;

(d) modifying and detecting the modulated optical probe pulse and converting the modulated optical probe pulse to electronic information; and (e) receiving and processing the electronic information to produce a microscopic image of the target.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 1B is a schematic illustration of a portion of an exemplary transmitted mode T-ray microscope embodiment similar to the system shown in FIG. 1A, in which the emitter includes an optical reflective coating;

FIG. 3 is a schematic illustration of a portion of an exemplary transmitted mode T-ray microscope embodiment comprising a CCD camera for detecting the optical beam;

FIG. 4 is an illustration of a portion of an exemplary reflected mode T-ray microscope embodiment;

DETAILED DESCRIPTION OF INVENTION

Figure 1A:
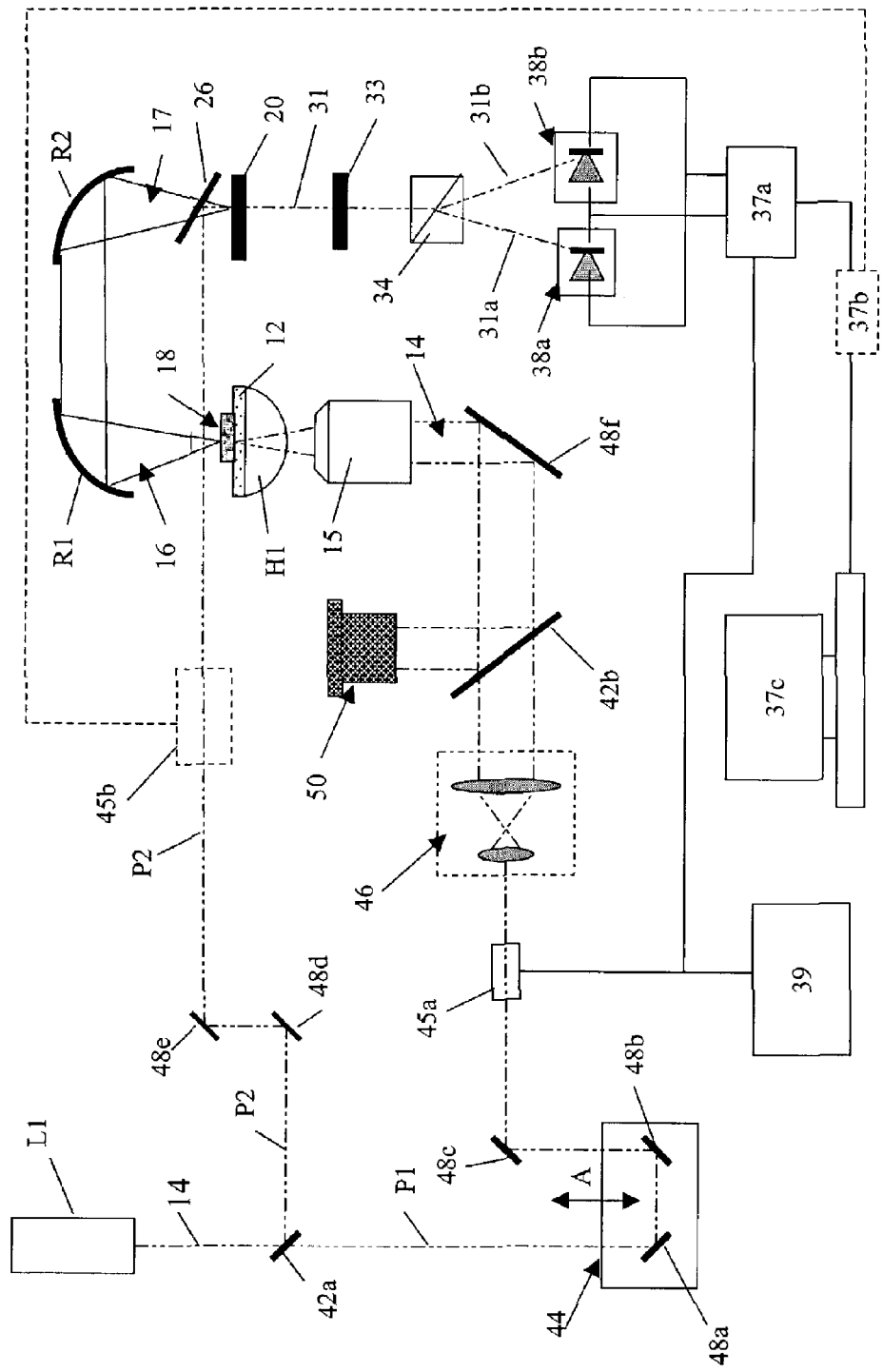
FIG. 1A is a schematic diagram of an exemplary T-ray microscope system.

Currently, there are two basic approaches for generating THz beams using ultrafast laser pulses: photoconduction and optical rectification. One preferred optical source for the generation of THz waves is an ultrafast Ti:sapphire laser having a pulse energy from nJ to $\mu$J and a pulse duration of 100 fs and a center wavelength at 800 nm. The photoconductive approach employs high-speed photoconductors as transient current sources for radiating antennas. The optical rectification approach uses electro-optic crystals as rectification media. Rectification can be a second order (difference frequency generation) or a higher order nonlinear optical process, depending on the optical power density.

Optical rectification is the inverse process of the electro-optic effect. In contrast to photoconducting elements where the optical beam functions as a trigger, the energy of THz wave radiation generated by the transient optical rectification process comes from the excitation laser pulse. The conversion efficiency ($10^{-4}$ to $10^{-6}$) depends on the value of the nonlinear coefficient and the phase matching condition. In the optical rectification mode, the THz pulse duration is comparable to the optical pulse duration, and the frequency spectrum is mainly limited by the spectral broadening of the laser pulse, as determined by the uncertainty principle.

Similar to the generation of THz waves, both photoconductive and electro-optic methods can be used to detect THz waves. Photoconductive antennas were first used to detect freely propagating THz waves, but electro-optic detection has more recently become widely used in many research laboratories due to its ultra-wide bandwidth and parallel imaging capability. THz wave transceivers, which alternately transmit THz radiation (by optical rectification) and receive the returned signal (by the electro-optic effect), have been recently developed, as disclosed in U.S. patent application Ser. No. 09/826,458, filed Apr. 5, 2001, by Zhang et al. and incorporated herein by reference. Transceivers provide known advantages in THz wave ranging, remote sensing, time-of-flight imaging, and tomographic imaging applications. Use of a transceiver is ideal for the measurement of THz waves reflected from a target. Compared to traditional THz tomography setups in reflection geometry, imaging systems with electro-optic transceivers are simpler and easier to align. In addition, the normal incidence of the THz beam on the sample can be maintained.

In an electro-optic sampling setup, the field-induced birefringence of the sensor crystal due to an applied electric field (THz wave), modulates the polarization ellipticity of an optical probe beam that passes through the crystal. The ellipticity modulation of the optical beam can then be polarization analyzed to provide information on both the amplitude and phase of the applied electric field. The balanced detection system analyzes a polarization change from the electro-optic crystal and correlates it with the amplitude and phase of the THz electric field. The time delay is provided by changing the relative length of the beam path between the THz radiation pulses and the optical probe pulses (pump-probe sampling method). Detection sensitivity is significantly improved by increasing the interaction length of the pulsed field and optical probe beam within the crystal, accomplished by using a thicker crystal. The signal-to-noise ratio of electro-optic detection can exceed 10,000:1.

With a Ti:sapphire laser as the optical source, an ideal crystal for THz generation and detection is zinc telluride (ZnTe) because ZnTe satisfies the phase matching condition (the group velocity of the optical beam at 800 nm equals the phase velocity of the THz wave at 2 THz). The analysis of the electro-optic tensor of zincblende crystals predicts that the best orientation to generate and detect THz waves in a ZnTe is the <110> cut. If optical sources with different wavelengths are used, the phase matching condition may be different, meaning that other electro-optical crystals may be more favorable. For example, GaAs is more favorable for the 1.5 $\mu$m optical beam and GaP is more favorable for the 1.3 $\mu$m optical beam.

Referring now to FIGS. 1A and 1B there are shown schematic diagrams of an exemplary transmitted mode microscope system of this invention. An electro-optic (EO) crystal 12, such as but not limited to ZnTe or LiNbO$_3$, is used to generate THz wave signals 16 from a laser pulse 14 focused by a lens or lens system 15 onto the crystal. A tissue sample 18 is directly mounted on the surface of EO crystal 12. As shown in FIG. 1B, EO crystal 12 may have a reflective coating 13b, such as but not limited to highly-reflective coating such as GaAs that blocks the optical portion of laser beam 14 from being transmitted through crystal 12. THz pulse 16 is generated in crystal 12 by optical rectification and detected by a THz wave detector crystal 20 by the electro-optic effect.

In the transmitted mode shown in FIG. 1A, the THz waves emitted by crystal 12 and transmitted through sample 18 are typically bounced off of one or more parabolic mirrors such as R1 and R2 and then directed to a separate THz detector 20. An optical probe pulse P2 is used for sampling the THz wave in the THz detector.

In the exemplary embodiment shown in FIG. 1A, pulse 14 from laser L1 is split by beam splitter 42a into a pump pulse P$_1$ and a probe pulse P$_2$. Pump pulse P$_1$ travels through delay stage 44 comprising mirrors 48a, 48b, 48c and is then directed into modulator 45a, such as an acousto-optic (AO) modulator, which is integrated with lock in amplifier 37a and function generator 39 as is explained in more detail below. Delay stage 44 provides a variable distance through which pulse P$_1$ travels by moving closer to and further away from splitter 42a along arrow A.

Pump pulse P$_1$ next is directed through beam expander 46 and is focused through objective lens system 15 and, optionally, through hemispherical lens H1 onto crystal 12. The reason for using a hemispherical lens or super-hemispherical lens in contact with crystal 12 is discussed later in this specification. Crystal 12 generates THz waves 16 that are transmitted through sample 18. Sample 18 is placed within THz radiation the near field area, shown as dotted line boundary NF in FIG. 1B. Near field is defined as a distance less than a wavelength of the THz radiation from the point of the THz radiation generation.

Between beam expander 46 and objective lens 15 may be beam splitters 42b and mirror 48f which allow a reflected optical view of sample 18 to be visualized through optical eye piece 50 of a standard optical microscope. It should be noted herein that flat mirrors 48a–48f and beam splitters 42a and 42b are illustrated herein as needed to show a logical schematic diagram. More or fewer mirrors and beam splitters may be provided, however, as is required or allowed the physical space provided for the microscope system.

The THz waves 16 transmitted through sample 18 are collimated and focused by parabolic mirrors R1 and R2 onto detector crystal 20 after passing through pellicle 26. Probe pulse P$_2$ is directed to pellicle 26, which is typically 2 to 4 microns thick such that the long wavelength of THz pulse 16 passes through pellicle 26 without reflection. In detector 20, the E-field of the THz waves 16 induces birefringence inside the ZnTe crystal of EO detector 20, which in turn tunes (changes the polarization of) probe pulse P$_2$ by modulating it to include a component proportional to the THz waves. Thus, optical pulse 31 leaving detector 20 contains information relating to THz waves 16.

A quarter waveplate 33, a Wollaston prism 34, and photodetectors 38a, 38b comprise a typical EO sampling system, which is known in the art. Quarter waveplate 33 changes the linear polarization of pulse 31 to a circular polarization. Wollaston prism 34 splits the circular polarization of pulse 31 back into linearly polarized pulses 31a and 31b, each polarized 90° relative to the other. Each pulse 31a and 31b is directed onto photo detectors 38a and 38b, respectively, which may be photodiodes. Photo detectors 38a and 38b are connected to circuitry (not shown), known in the art, which subtracts the waveform of pulse 31b from the waveform of pulse 31a to eliminate the common current with reduced noise. The modulation of pulse P$_2$ by output pulse 16 within EO detector 20 can be detected because the intensity components in pulses 31a and 31b proportional to the THz electric field have the same value but opposite sign. Thus, the change in probe pulse P$_2$ induced by THz waves 16 is doubled after subtraction of pulse 31a from pulse 31b.

The sensitivity of the T-ray microscope may be improved using any method for improving signal-to-noise ratio (SNR) known in the art. A number of SNR improvement techniques for THz systems are known in the art. An exemplary single lock-in amplifier system, comprising lock-in amplifier 37a, modulator 45a, and function generator 39 is shown in FIG. 1A. As is known in the art, pump pulse P1 may be modulated on/off with modulator 45a in accordance with a square wave function generated by function generator 39 that is synchronized with lock-in amplifier 37 to reduce noise.

Another known noise reduction technique comprises differential spectroscopy, which is described by Zhiping Jiang, Ming Li, and X.-C. Zhang, in "Dielectric constant measurement of thin film by differential time-domain spectroscopy," Appl. Phys. Lett., 76, 3221(2000), incorporated herein by reference. Another noise reduction technique is a double modulation technique, described generally by S. V. Frolov and Z. V. Verdeny in "Double-modulation electro-optic sampling for pump-and-probe ultrafast correlation measurement," Review of Scientific Instruments, 69, 1257 (1998), incorporated herein by reference. Differential spectroscopy allows measurement of a change in T-ray field transmission ($\Delta$T/T) as low as $10^{-5}$, and the two-frequency modulation and double lock-in amplifier methods may further improve the signal-to-noise ratio by a factor of 10.

Optional components capable of converting the single lock-in amplifier set-up shown in FIG. 1A to a two-frequency modulation and double lock-in amplifier set-up are shown in dashed lines. The two-frequency modulation and double lock-in amplifier set-up provides means for modulating the T-ray and optical probe beams at 1 MHz and 1 kHz rates, respectively. This method greatly reduces noise from laser power fluctuations, mechanical vibration and other external noises. In such a system, modulator 45 may comprise a RF modulator (MHz) and lock-in amplifier, 37b may comprise an RF lock-in amplifier, and a galvanometer 45b and audio frequency (AF) lock-in amplifier may be used to produce and detect the optical pulse modulation (kHz), respectively. The dual modulation method, compared to the use of a single lock-in amplifier method, overcomes low frequency external noise at kHz frequencies, but is still benefited by the better system performance of the AF amplifier. A computer 37c may be used to control the system, process imaging data and display captured images.

The physical relationships among the sample, emitter, detector, and probe beam for a transmission-mode system are not limited to the layout schematically shown in FIGS. 1A and 1B. What is important is to create an arrangement where the sample is in a THz near field (shown as a dotted line boundary NF in the figures) and either the target sample is scanned in the near field by the THz beam generated by an optical pump beam spot whose diameter is reduced to substantially the theoretical diffraction limits, or, in an alternative arrangement discussed later in this specification, by placing the target sample on a detector surface such that the THz radiation transmitted through the target sample to the detector is scanned by an optical probe spot size again reduced to substantially its theoretical limits, again as discussed later on in this description.

Figure 2A:
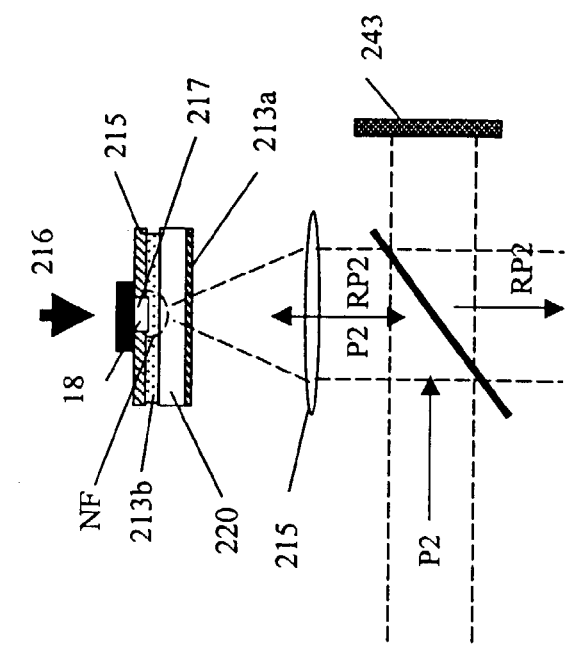
FIG. 2A is a schematic illustration of a portion of an exemplary transmitted mode T-ray microscope embodiment in which the sample is placed on the detector.

For example, as shown in FIG. 2A, the system may be set up with sample 18 disposed on THz detector 220 rather than on THz emitter (not shown) shown in FIG. 1A. In such a layout, the emitter crystal and collimating parabolic mirrors (not shown) are located before sample 18 to create a THz pulse 216 that is transmitted through the sample into the detector 220. The probe beam P2 is reflected off beam splitter 242 through lens 215 from below detector 220. The sample is so located that the THz near field of radiation through the sample enters the detector crystal and is probed by the probe beam P2 which is again focussed to a substantially diffraction limited spot. Preferably, a hemispherical or super-hemispherical lens H2 shown in dotted line is used to focus the probe beam onto the detector.

Detector crystal 220 preferably has an anti-reflective coating 213a on the bottom surface and reflective coating 213b on the top surface. The coatings help prevent optical loss in the crystal and leakage of the optical beam into the tissue sample. THz pulse 216 as modulated by sample 18 modulates the reflection of optical probe beam RP2 off of reflective coating 213b, thereby creating a modulated optical beam that passes through beam splitter 242 to the detection optics (not shown). The components of the system not shown in FIG. 2A may be the same or similar to those shown in FIG. 1A, or may be set up in accordance with any THz system known in the art. Because of the use of beam splitter 242, beam dumping elements 243 are provided, as are known in the art, to dispose of the portion of the probe beam P2 transmitted through beam splitter 242.

Figure 2B:
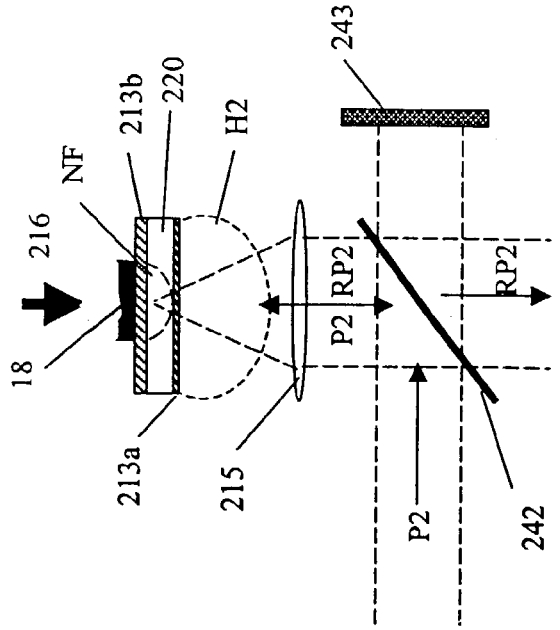
FIG. 2B is a schematic illustration of a portion of an exemplary transmitted mode T-ray microscope embodiment in which the sample is placed on a detector having a metallic film and aperture.

As shown in FIG. 2B, detector crystal 220 may also comprise a conductive metallic film 215, such as but not limited to a highly-conductive metallic film such as gold, having at least one aperture 216, over reflective coating 213b on the top surface of emitter crystal 218. Metallic film 215 and aperture 216 limit the amount of THz signal passed through the metallic film to a beam the size of the aperture. This is particularly helpful for a detector crystal 220 that has a thickness greater than the dimensions of the sample. Although shown in FIG. 2B with both metallic film 215 and coatings 213a and 213b, detector crystal 220 may be provided with only the coatings 213a and 213b (such as is shown in FIG. 2A) or only one of the coatings (not shown), with only the metallic film 215 (not shown), or with no coatings or films at all. The use of various coatings, however, is helpful in improving the overall system performance.

To collect information across a desired length and width of a sample, the EO crystal, the sample, or the THz beam can be scanned laterally to obtain a two-dimensional image. As a practical matter, because sample 18 is placed on the top of EO crystal 12, both are typically scanned together. For example, two-dimensional scanning may be performed by using an x-y mechanical stage with a step size of 0.1 $\mu$m. The use of a highly focussed optical spot rather than THz radiation in the present invention permits higher resolution limited by the wavelength of the optical beam rather than the THz radiation wavelength. Thus, sub-micron spatial resolution is achievable even though the imaging wavelength is about 300 $\mu$m at 1 THz.

Another method of getting two-dimensional information with a transmission mode microscope system is schematically shown in FIG. 3. This system has a similar physical layout to that shown in FIG. 2A, without the focal lens between the probe beam and the beam splitter. Thus, probe beam P2 has a relatively wide waist, providing a modulated optical beam 331 having a similarly large waist. Modulated optical beam 331 then passes through a polarizer 300 and focal lens 301 and is ultimately read by a charge-coupled device (CCD) camera 302. The use of CCD cameras for two-dimensional imaging is discussed generally by Wu, Hewitt, and Zhang, in "Two-dimensional electro-optic imaging of THz beams," Appl. Phys. Lett. 69 (8) pp. 1026–1028 (1996), incorporated herein by reference.

The spatial resolution in the above systems is typically limited only by the optical focal size of the laser on the crystal and can be less than 1 $\mu$m due to the large refractive index of 2.8 for ZnTe under a moderate optical power, and is independent of the THz wave wavelength.

When a Ti:sapphire laser with $\lambda=0.8$ $\mu$m is used as the optical source, the smallest optical focal spot a in the air is calculated by the standard equation of $d=1.22\lambda 2f/D$, where d is the spot diameter, f is the wavelength, D is the beam diameter, and D/2f is the numerical aperture NA of the microscope objective lens. Assuming the ideal case with NA=1, then d=1 $\mu$m. One way to achieve sub-micron lateral resolution is to focus the optical beam into a high refractive index medium. The refractive index of the ZnTe is greater than 1; therefore, the focal spot in a ZnTe must be smaller than that in air by the factor of the refractive index value. It is difficult, however, to achieve a much smaller focal spot by directly focusing a laser beam from the air into a ZnTe plate, because of the change of the numerical aperture after the optical refraction at the interface of the ZnTe in accordance with Snell's Law.

An alternate embodiment of this invention is to use a T-ray microscope in a reflection mode. In a reflection mode, the EO crystal on which the sample is mounted acts as both an emitter and a detector, otherwise known as a transceiver.

THz transceiver systems are described generally in U.S. patent application Ser. No. 09/826,458, filed Apr. 5, 2001, by X. C. Zhang et al., incorporated herein by reference.

A pertinent portion of an exemplary reflected mode microscope 410, is shown schematically in FIG. 4. In the reflected mode microscope 410, both the THz emitter and receiver functions are combined in a single transceiver crystal 412, such as a <110> cut ZnTe crystal, in the near-field range NF. In the transceiver crystal 412, both pump pulse P1 and probe pulse P2, having different wavelength between one and the other are transmitted through beam splitter 442 and then focused by focal lens 415 through hemispherical lens 428 onto crystal 412, which generates THz waves. The numerical apertures of focal lens 415 and hemispherical lens 428 are identical, and the refractive index n of hemispherical lens 428 and crystal 412 are the same resulting in an expected overall improvement in spot size reduction of 1/n as compared with the case of air, that is where there is no hemispherical lens present.

In the case of ZnTe, n=2.8 the expected spot diameter reduction when compared to no hemispherical lens present would be of the order of 1/2.8 (or about 0.36 times the diameter of the spot).

Figure 5:
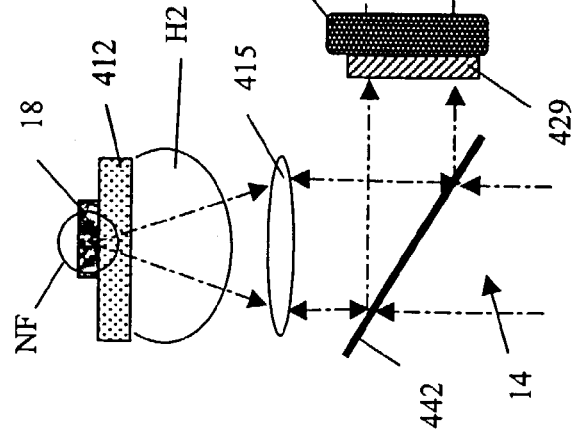
FIG. 5 is an illustration of the same portion of the exemplary reflected mode T-ray microscope embodiment showing the use of a super-hemispherical lens in accordance with an alternate embodiment of the present invention.

Preferably a super-hemispherical lens H2 is used as a solid immersion lens instead of the hemispherical lens H1 shown in FIG. 4, as shown in FIG. 5. The use of the super-hemispherical lens can improve NA and also decrease wavelength resulting in an overall minimum focused spot size reduction of $1/n^2$ compared to air, where n is the refractive index of the super hemispherical lens and the terahertz transceiver. When a super-semispherical lens is used instead of the hemispherical ZnTe example above, one may expect a spot diameter reduction of the order of 0.13D where D is the diameter possible without the super-hemispherical lens.

The different wavelength of the pump and probe beams is used to separate the pump beam from the probe beam after the beams reflect from the crystal/tissue interface.

The pump pulse generates the THz wave in the ZnTe crystal by optical rectification. The THz waves that reflect off of tissue sample 418 modulate the optical component of the reflected probe pulse. The modulated optical probe pulse (as well as a reflected portion of the optical pump pulse) are transmitted back through lenses 428 and 415 and are reflected off of beam splitter 442. Filter 429 located in front of polarizer 430 separates the pump beam from the probe beam and polarizer 430 also analyzes the polarization change of the modulated probe beam induced by the THz waves. The analyzed optical pulse 431 is focused by lens 432 onto diode 438, where the signal is optically received. Because target sample 18 is placed on top of transceiver crystal 412, the THz wave is generated and detected at the same focal spot within the transceiver crystal 412. The T-ray imaging spot on the tissue is comparable to the focal spot of the optical beam. The reflected mode geometry allows measurements to be made in-vivo.

The optical beam is focused in the ZnTe through the matching refractive index lens to a spot size comparable to a 1.22λ/n (assuming NA=1). If λ=0.8 μm and n=2.8, in theory the focal spot can be a small as 0.35 μm. A smaller focal spot can be provided by using a shorter optical wavelength, such as the second harmonic wave from the Ti:sapphire laser.

For high precision measurements, the THz wave microscope or a portion thereof, particularly at least the target, the THz emitter, and the THz sensor, may be placed in a vacuum chamber, for instance having a pressure of $10^{-4}$ Torr. The vacuum system may be especially important for sensing and imaging studies of nanolayer biomedical samples (such as monolayer DNA and protein) because any guest molecules from the air might otherwise contaminate the sample. The vacuum chamber also allows atmospheric moisture and other contaminant gases to be removed.

Due to the intense power density at an optical focal spot (micron or sub-micron), some higher order nonlinear phenomena other than optical rectification may limit THz wave generation and detection. For example, two-photon absorption (a third order nonlinear optical effect) in ZnTe generates free carriers. At a tight focal spot, extremely high free-carrier density changes the ZnTe local conductivity, screens the THz wave, and saturates the THz wave field. A reduction in optical peak power may be accommodated by increasing the pulse repetition-rate. The trade-off between the average power and the peak power may be optimized to provide efficient THz wave generation.

The microscope system may be calibrated using several commonly used imaging calibration charts, including the U.S. Air Force Target, the IEEE Chart, and the FBI standard chart, which are well known in the art. All of these imaging charts contain micron size structure patterns and may be placed directly on the top of the EO crystal. It has been observed that the imaging resolution is different for the polarization of the THz wave parallel or perpendicular to a metallic line. This is due to the induced current in the metallic line. Charts fabricated on dielectric films may avoid such effects.

The THz microscope may dramatically enhance pathological inspection and analysis of tissues. In addition to helping in diagnosis, it may also be useful in helping to discover causes of the pathology, by giving new molecular-level information that is linked with morphological changes in the tissue/cells. The microscope may also be used to investigate rapid biochemical responses to selected stimuli, giving new insight into biological processes.

The microscope may be applied to tissue characterization, starting from the biomolecules and monolayers of cells. A detailed analysis of specific changes in spectroscopic signatures with subtle changes in molecular structure or composition in the biomolecules may be compiled.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A microscope for producing an image of a target, the microscope comprising:

a source for providing an optical pump pulse and an optical probe pulse;

a THz emitter for emitting THz radiation a THz detector having a first surface and a second surface substantially parallel and opposite said first surface;

means for impinging said pump beam onto said THz emitter;

means for directing said THz radiation through said THz detector second surface;

means for impinging said probe beam onto said detector through said first surface of said detector;

wherein said means for impinging said probe beam comprise an optical focusing means for focusing said probe beam to a substantially optical wave length limited spot size; and wherein said second surface of said detector is adapted to receive a sample within a near field of said THz radiation.

2. The microscope of claim 1, wherein the THz emitter and the THz detector comprise a single THz transceiver.

3. The microscope of claim 2, and wherein said pump beam and said probe beam impinge on said transceiver along coincident paths.

4. The microscope according to claim 2 wherein said transceiver modulates said probe beam and wherein said microscope further includes noise reduction means.

5. The microscope according to claim 4 wherein said noise reduction means comprises a first modulator for modulating the pump beam at a first frequency and the probe beam at a second frequency said second frequency being lesser than said first frequency.

6. The microscope of claim 1 further comprising reflector means for receiving THz radiation emitted from said emitter and for focusing said THz radiation onto said detector after said radiation has transited a sample placed on said detector second surface.

7. The microscope according to claim 1 wherein said detector modulates said probe beam and wherein said microscope further includes optical detection means for detecting said modulated probe beam.

8. The microscope according to claim 7 wherein said optical detection means comprises a CCD camera.

9. The microscope according to claim 7 wherein said optical detection means comprises a photodetector.

10. A microscope for producing an image of a target, the microscope comprising:
a source for providing an optical pump pulse and an optical probe pulse;
a THz emitter for activation by the optical pump pulse to emit a THz pulse that irradiates the target to form of a target-modified THz pulse said THz emitter comprising an EO crystal having first, pump beam side, surface and a second, target side surface, opposite said first surface the target side surface adapted to support said target within a near field of said THz irradiated pulse;
a focal lens for focusing at least said pump beam onto said THz emitter;
one of a hemispherical lens or super-hemispherical lens between said focal lens and said emitter in contact with said first surface;
a THz detector for modulating the probe pulse with the target-modified THz pulse to create a modulated optical probe pulse characteristic of the target;
an optical detection system for modifying and detecting the modulated optical probe pulse and converting the modulated optical probe pulse to electronic information;
a processor for receiving the electronic information and producing an image of the sample using the electronic information.

11. The microscope according to claim 10 wherein said one of said hemispherical lens or super hemispherical lens has an index of diffraction and said EO crystal also has a refractive index, and wherein the refractive index of said one of said hemispherical lens or super hemispherical lens is substantially the same as the refractive index of said EO crystal.

12. The microscope of claim 10, wherein the THz emitter and the THz detector comprise a single THz transceiver, and the target-modified THz pulse comprises a reflected component.

13. The microscope of claim 12 wherein both the pump beam and probe beam are focused through said focal lens onto the THz transceiver.

14. The microscope of claim 10, wherein the THz emitter comprises a first EO crystal and the THz detector comprises a second EO crystal, and the target-modified THz pulse comprises a transmitted component.

15. The microscope of claim 14, wherein the target is placed on a top surface of the THz emitter, and the pump beam is directed to the THz emitter from underneath the emitter.

16. The microscope of claim 14, wherein the target is placed on a top surface of the THz detector, the THz pulse is directed to the THz detector from above the detector, and the probe beam is directed to the THz detector from underneath the detector.

17. The microscope of claim 16, further comprising a conductive coating on the second surface of said EO crystal, and at least one aperture in the conductive coating.

18. The microscope of claim 10 further comprising noise reduction components.

19. The microscope of claim 18, wherein the noise reduction components comprise a first modulator for modulating the pump beam at a first frequency and integrated with a first lock-in amplifier positioned between the optical detector and the processor.

20. The microscope of claim 19, wherein the noise reduction components further comprise a second modulator for modulating the probe beam at a second frequency and integrated with a second lock-in amplifier connected in series with the first lock-in amplifier.

21. The microscope of claim 20, wherein the first frequency is greater than or equal to about 1 MHz and the second frequency is greater than or equal to about 1 kHz.

22. The microscope of claim 10 further comprising a delay stage positioned in a pathway of one of the pump pulse or the probe pulse for enabling characterization of a complete waveform of the THz pulse.

23. The microscope of claim 10, wherein the optical detection system comprises a Charge Coupled Device (CCD) camera.

24. The microscope of claim 10 wherein said EO crystal second surface lies in an x-y plane and the microscope further comprises means for scanning the target across said x-y plane.

25. The microscope of claim 10 wherein the focal lens comprises an optical microscope objective in optical alignment with an optical microscope eyepiece to provide optical monitoring of the sample.

26. The microscope of claim 10, wherein the source is a ultra fast laser.

27. The microscope of claim 26 wherein the laser is a Ti:sapphire laser.

28. The microscope according to claim 10 wherein said THz detector is also an EO crystal.

29. The microscope of claim 28, wherein the EO crystal comprises ZnTe.

30. The microscope of claim 28, wherein the EO crystals comprise $LiNbO_3$.

31. The microscope of claim 10, further comprising a vacuum chamber in which at least the target, the THz emitter, and the THz detector are located.

32. The microscope of claim 10, wherein at least one of said first and second surfaces of the EO crystal further comprise an optically-reflective coating thereon.

33. The microscope of claim 32, wherein the optically-reflective coating comprises GaAs.

34. The microscope of claim 33, wherein the EO crystal further comprises a conductive coating over the reflective coating, the conductive coating having at least one aperture therein.

35. The microscope of claim 34, wherein the conductive coating comprises gold.

36. A method for a microscopic examination of a target using T-rays, the
- providing an optical pump pulse and an optical probe pulse along a pump optical path and a probe optical path and impinging said optical pump pulse onto a THz emitter comprising an EO crystal thereby emitting a THz radiation pulse from said THz emitter;
- positioning said target on a first surface of a THz radiation detector EO crystal and impinging said THz radiation pulse onto said target and said detector transmitting or reflecting the THz pulse through or off of the target, creating a target-modified THz pulse;
- transmitting said optical probe pulse along a probe optical path and focusing said optical probe pulse through an optical means to an optical spot size limited by the optical probe pulse wavelength on said first surface of said detector within a near field of said THz radiation impinged on said target;
- modulating the focused optical probe pulse with the target-modified THz pulse in said THz detector EO crystal to create a modulated optical probe pulse characteristic of the target with a resolution substantially the same as said optical spot size;
- modifying and detecting the modulated optical probe pulse and converting the modulated optical probe pulse to electronic information;
- receiving and processing the electronic information to produce a microscopic image of the target.

37. A method for a microscopic examination of a target using T-rays, the method comprising:
- providing an optical pump pulse and an optical probe pulse along a pump optical path and a probe optical path; focusing said optical pump pulse onto a THz emitter comprising an EO crystal, by transmitting said optical pump pulse along said pump optical path through a focal lens and one of a hemispherical or super hemispherical lens located on a first surface of said EO crystal thereby emitting a THz pulse from said THz transmitter wherein said hemispherical or super hemispherical lens has a refractive index substantially the same as the refractive index of said EO crystal;
- positioning said target in a near field of said THz pulse and transmitting or reflecting the THz pulse through or off of the target, creating a target-modified THz pulse;
- modulating the probe pulse with the target-modified THz pulse in a THz detector EO crystal to create a modulated optical probe pulse characteristic of the target;
- modifying and detecting the modulated optical probe pulse and converting the modulated optical probe pulse to electronic information;
- receiving and processing the electronic information to produce a microscopic image of the target.

38. The method according to claim 37 wherein the THz emitter and the THz detector comprise a THz transceiver on a single EO crystal.

* * * * *